(12) United States Patent
Miller

(10) Patent No.: US 10,207,073 B2
(45) Date of Patent: Feb. 19, 2019

(54) RESPIRATORY APPARATUS

(75) Inventor: Andrew Neil Miller, Crowthorne (GB)

(73) Assignee: Intersurgical AG, Vaduz (LI)

(*) Notice: Subject to any disclaimer, the term of this patent is extended or adjusted under 35 U.S.C. 154(b) by 500 days.

(21) Appl. No.: 13/985,006

(22) PCT Filed: Feb. 20, 2012

(86) PCT No.: PCT/GB2012/050373
§ 371 (c)(1),
(2), (4) Date: Aug. 12, 2013

(87) PCT Pub. No.: WO2012/114088
PCT Pub. Date: Aug. 30, 2012

(65) Prior Publication Data
US 2013/0319409 A1    Dec. 5, 2013

(30) Foreign Application Priority Data
Feb. 21, 2011    (GB) .................... 1102942.8

(51) Int. Cl.
*A61M 16/08*    (2006.01)
*G01F 15/18*    (2006.01)
(Continued)

(52) U.S. Cl.
CPC ........ *A61M 16/08* (2013.01); *A61M 16/0816* (2013.01); *A61M 16/0833* (2014.02);
(Continued)

(58) Field of Classification Search
CPC .......... A61M 39/10; A61M 2039/1094; A61M 39/02; A61M 2202/0482; A61M 16/0463;
(Continued)

(56) References Cited

U.S. PATENT DOCUMENTS 4,046,139 A * 9/1977 Horn .................... A61B 1/2676
128/207.15
4,270,778 A * 6/1981 Brownell .......... A61M 16/0463
128/207.14
(Continued)

FOREIGN PATENT DOCUMENTS

EP    1374940 A2    1/2004
EP    1430923 A2    6/2004
(Continued)

OTHER PUBLICATIONS

International Search Report for PCT/GB2012/050373, filed Feb. 20, 2012, (dated Jun. 28, 2012).
(Continued)

*Primary Examiner* — Annette Dixon
(74) *Attorney, Agent, or Firm* — LeClairRyan PLLC

(57) ABSTRACT

A component (10) of a respiratory apparatus is disclosed, which comprises a gas passageway defined by an enclosing wall (20,30), and a port (40) in the enclosing wall (20,30) adapted to receive an ancillary device (60). The component (10) also includes a retaining arm (50) that is movable between an open configuration in which an ancillary device (60) may be engaged with the port (40), and a retention configuration in which the retaining arm (50) acts, in use, to resist removal of the ancillary device (60) from the port (40).

32 Claims, 2 Drawing Sheets

(51) Int. Cl.
*A61M 16/16* (2006.01)
*A61M 16/00* (2006.01)

(52) U.S. Cl.
CPC ...... *A61M 16/0841* (2014.02); *A61M 16/161* (2014.02); *G01F 15/18* (2013.01); *G01F 15/185* (2013.01); *A61M 2016/003* (2013.01); *A61M 2205/3368* (2013.01)

(58) Field of Classification Search
CPC .......... A61M 16/0488; A61M 16/0497; A61M 16/08; A61M 16/0816; A61M 16/0825; A61M 16/0833; A61M 2025/024; A61M 2039/1027; A61M 2039/1044; A61M 2039/1066; A61M 2039/1072; A61M 2039/1077; A61M 2205/195; A61M 2205/197; A61M 39/1011; A61M 39/14; A61M 39/26; A61J 15/0026; A61J 15/0092; A61J 15/00; B60H 3/00; F16L 27/093; F16L 27/12; F16L 3/00; F16L 35/00; F16L 37/00; F16L 37/0985; F16L 37/133; F16L 41/005; F16L 55/005; H04N 5/4446; H04N 7/102; Y10S 128/26; Y10S 285/902; Y10S 285/921; Y10S 604/905; Y10T 137/71; Y10T 24/1406; Y10T 24/141; Y10T 24/1498; Y10T 24/153; Y10T 24/3444; Y10T 24/45901; Y10T 29/49947; Y10T 292/48
USPC ........... 128/202.27, 202.28, 202.29, 207.14, 128/207.15, 206.29, 200.26, 912, 204.18, 128/869, 876
See application file for complete search history.

(56) References Cited

U.S. PATENT DOCUMENTS

| | | | | | |
|---|---|---|---|---|---|
| 4,307,903 | A | * | 12/1981 | Wallace | A61M 16/08 128/207.14 |
| 4,580,556 | A | * | 4/1986 | Kondur | 128/206.28 |
| 4,951,661 | A | * | 8/1990 | Sladek | A61M 16/0808 128/202.27 |
| 5,057,093 | A | * | 10/1991 | Clegg et al. | 604/535 |
| 5,322,073 | A | * | 6/1994 | Michels | A61M 39/1011 128/869 |
| 5,474,063 | A | | 12/1995 | Reindeau | |
| 5,554,140 | A | * | 9/1996 | Michels | A61M 39/1011 604/261 |
| 5,797,634 | A | * | 8/1998 | Bonser | F16L 37/0985 285/319 |
| 5,803,509 | A | * | 9/1998 | Adams | A61M 39/1011 285/114 |
| RE39,724 | E | | 7/2007 | Gradon et al. | |
| 7,263,994 | B2 | | 9/2007 | Gradon et al. | |
| 8,858,532 | B2 | * | 10/2014 | Tsunematsu et al. | 604/535 |
| 2005/0033237 | A1 | * | 2/2005 | Fentress | A61M 25/0009 604/165.03 |
| 2005/0034729 | A1 | * | 2/2005 | Dombrowski | A61M 16/0488 128/207.14 |
| 2009/0282896 | A1 | * | 11/2009 | Tappehorn | A61B 5/087 73/23.3 |
| 2009/0326481 | A1 | * | 12/2009 | Swisher et al. | 604/246 |

FOREIGN PATENT DOCUMENTS

| | | | | |
|---|---|---|---|---|
| GB | 2272296 | A | | 5/1994 |
| JP | H03-106371 | | | 5/1991 |
| JP | 2004033788 | A | | 2/2004 |
| JP | 2008-511341 | | | 4/2008 |
| WO | 2004108218 | A1 | | 12/2004 |
| WO | WO 2004108218 | A1 | * 12/2004 | ........... A61M 16/08 |
| WO | 2005079670 | A1 | | 9/2005 |
| WO | 2006131719 | A1 | | 12/2006 |

OTHER PUBLICATIONS

Search Report for GB1202864.3, filed Feb. 21, 2011, (dated May 17, 2012).

* cited by examiner

RESPIRATORY APPARATUS

This application is a national stage application, submitted under 35 U.S.C. § 371, of PCT Application No. PCT/GB2012/050373, filed Feb. 20, 2012, which claims the priority benefit of Great Britain Application No. 1102942.8, filed Feb. 21, 2011.

FIELD OF THE INVENTION

The present invention relates to respiratory apparatus and, in particular, components of respiratory apparatus having a port into which an ancillary device, such as a sensor probe, is inserted.

BACKGROUND OF THE INVENTION

Medical respiratory apparatus typically includes a breathing circuit that is composed of a number of cooperating components, which connect together to form gas passageways that carry inhalation and/or exhalation gases. It is often desired to engage ancillary devices with the gas passageways of the breathing circuit, for example to monitor the temperature, flow rate and/or humidity of the gases in the breathing circuit. In particular, the ancillary devices are typically sensor probes, which are exposed to the flow of gas within the gas passageways of the breathing circuit.

In order to enable engagement of ancillary devices with the gas passageways of a breathing circuit, a suitable port is typically provided in one or more of the components that form the breathing circuit, the port being adapted to receive the ancillary device, such that the ancillary device is exposed to the gas within the breathing circuit. The port typically has the form of an opening in a wall of a flow passageway, with a cylindrical sleeve projecting outwardly therefrom. The cylindrical sleeve is typically adapted to receive the ancillary device with an interference fit, such that the ancillary device is exposed to the flow of gas within the breathing circuit. However, in view of the interference fit being the only means by which the ancillary device is retained, there may be a risk of dislodgement of the device from the port, and hence this conventional arrangement is not entirely satisfactory.

In an alternative arrangement, WO2004/108218 is arranged to secure the ancillary device in the opening by providing the opening with a resilient retaining arm that engages a corresponding ledge on the body of the ancillary device, with a snap-fit, to retain the ancillary device in the port. However, this arrangement requires the ancillary device to have a particular ledge formation for engagement with the retaining arm, and also makes insertion and removal of the ancillary device cumbersome for a user.

In addition, some types of ancillary devices must be disposed at a particular orientation, or within a particular range of orientations, relative to the direction of gas flow in order to function effectively. A particular example of this type of ancillary device is a flow sensor probe. Conventional arrangements for retaining and orientating a flow sensor probe comprise a cylindrical port for receiving the probe with an interference fit, and accompanying formations that engage with a portion of the probe during insertion, so as to require the probe to be in a particular orientation in order to be fully engaged with the port.

However, none of these types of arrangements have been found to be entirely satisfactory. In particular, the component disclosed in EP1374940 is arranged to orientate a flow sensor probe using a V-shaped locating projection on the probe, which is received within a corresponding V-shaped locating depression in the wall of the port with which the probe engages. The probe is particularly liable to be dislodged in this arrangement. In addition, the component disclosed in US2009/0282896 is arranged to orientate a flow sensor probe by providing a wall section adjacent to the port, which determines the orientation of the probe. In particular, the wall section is adapted to impinge on the housing of the probe, and hence prevent engagement of the probe with the port, unless the probe has a particular orientation relative to the port, and hence relative to the direction of gas flow.

There has now been devised an improved component of a respiratory apparatus which overcomes or substantially mitigates the above-mentioned and/or other disadvantages associated with the prior art.

SUMMARY OF THE INVENTION

According to a first aspect of the invention, there is provided a component of a respiratory apparatus comprising a gas passageway defined by an enclosing wall, a port in the enclosing wall adapted to receive an ancillary device, and a retaining arm that is movable between an open configuration in which an ancillary device may be engaged with the port, and a retention configuration in which the retaining arm acts, in use, to resist removal of the ancillary device from the port.

The component of a respiratory apparatus according to the invention is advantageous principally because the retaining arm resists removal of the ancillary device from the port, and hence may improve the security with which the ancillary device is retained in the port relative to prior art arrangements. Furthermore, the present invention enables the forces of engagement between the ancillary device and the port itself to be reduced, whilst still providing secure retention of the ancillary device, thereby facilitating insertion and intentional removal of the ancillary device during use.

The port preferably includes an opening in the enclosing wall through which the ancillary device extends into the interior of the gas passageway, or through which the ancillary device is exposed to the interior of the gas passageway. The opening is most conveniently a generally circular aperture.

The port preferably includes formations that maintain the ancillary device in alignment with an engagement axis, ie the axis along which the ancillary device engages the port. In particular, the port preferably includes an engagement sleeve adapted to receive the ancillary device. The engagement sleeve is most conveniently generally cylindrical in form. The engagement sleeve may be formed by a generally cylindrical collar that is upstanding from the enclosing wall at the periphery of the opening. The engagement sleeve is preferably adapted to receive the ancillary device with a close fit.

The port may be adapted to resist withdrawal of the ancillary device from the port, following engagement. The port may also, or instead, be adapted to resist lateral and/or rotational movement of the ancillary device following engagement. In addition to supplementing the resistance to removal of the ancillary device provided by the retaining arm, these features may in combination, or individually, maintain the ancillary device in a position suitable for engagement with the retaining arm, thereby facilitating assembly of the respiratory apparatus including the ancillary device.

The port may therefore be adapted to receive the ancillary device with an interference or frictional fit. The port may have a tapered interior surface, eg of generally frusto-conical form, to facilitate engagement of the ancillary device with the port. The port may include an indicator to facilitate alignment of the ancillary device within the port.

The retaining arm may be flexible in form. However, more preferably, the retaining arm is sufficiently rigid that its shape is substantially the same in both the open and retention configurations.

The retaining arm is preferably arranged not to impede engagement of an ancillary device with the port in its open configuration, and most preferably not to contact the ancillary device during engagement. The retaining arm may be retained in the open configuration until a user manually moves the retaining arm into its retention configuration. For example, the retaining arm may be at rest in the open configuration.

The retaining arm is preferably rotatable between the open and retention configurations. The angle of rotation between open and retention configurations is preferably at least 30°, more preferably at least 60°, and most preferably at least 90°. The retaining arm is preferably rotatably mounted at one end to an exterior surface of the component, such that the retaining arm is pivotable about that end. The retaining arm may be guided into the retention configuration. In particular, the retaining arm is preferably hingedly mounted to an exterior surface of the component. The retaining arm is preferably engaged with an exterior surface of the ancillary device in the retention configuration.

In presently preferred embodiments, the retaining arm is in contact with an exterior surface of the ancillary device in the retention configuration. The retaining arm preferably grips or captivates the ancillary device in the retention configuration.

For example, at least a portion of the retaining arm may be formed of a resilient material and adapted to receive at least a portion of the ancillary device therewithin, such that receiving the ancillary device within the resilient portion of the retaining arm causes the resilient portion to deflect to accept the ancillary device during engagement, the resilient portion acting to grip or captivate the ancillary device on full engagement of the retaining arm with the ancillary device. The retaining arm may engage the ancillary device with a snap fit.

The retaining arm may be adapted to resist removal of the ancillary device from the port by location of a retaining portion of the arm on an opposing surface of the ancillary device relative to the port. In the retention configuration, a portion of the retaining arm may be located directly opposite the port. In addition, or alternatively, in the retention configuration, a portion of the retaining arm may extend in a plane that is substantially parallel to the plane in which the entrance to the port lies, and this retaining portion may substantially face the entrance to the port.

In order to achieve this arrangement, the retaining arm may have a curved portion, the curved portion being adapted, in use, to engage the ancillary device. In one embodiment, the retaining arm is generally arcuate in overall shape. In this arrangement, the retaining arm resisting removal of the ancillary device from the port may be achieved with or without the retaining arm gripping or captivating the ancillary device in the retention configuration. In particular, in presently preferred embodiments, the retaining arm may be arranged to remain in the retention configuration, and in particular in engagement with the ancillary device, on movement of the ancillary device in the direction of disengagement from the port, without the retaining arm gripping or captivating the ancillary device. For example, the force applied by the ancillary device on the arm may be at an angle that does not result in rotation of the retaining arm to its open configuration.

The retaining arm is preferably rotatable about an axis that is generally perpendicular to the engagement axis of the port. The axis of rotation is preferably offset laterally from the engagement axis of the port, and may also be offset longitudinally from the entrance to port. The retaining arm may be hingedly mounted to a portion of the component that extends from the wall of gas passageway, most preferably generally aligned with a diametric plane of the gas passageway that is generally perpendicular to the engagement axis of the port. The retaining arm may be hingedly mounted to a mount, which may have the form of a web.

The retaining arm may include formations that facilitate movement of the retaining arm by the user, and in particular facilitate disengagement of the retaining arm from the ancillary device in the retention configuration. For example, the retaining arm may include an end portion that projects outwardly relative to the ancillary device in the retention configuration, most preferably on an opposing side of the ancillary device relative to the rotatably mounted end of the retaining arm.

The retaining arm is preferably adapted to at least partially determine the orientation of the ancillary device relative to the port in the retention configuration. In particular, the retaining arm may be adapted to permit orientation of the ancillary device in a single pre-determined orientation, or in a limited number of discrete pre-determined orientations. Alternatively, or in addition, the retaining arm may be adapted to permit orientation of the ancillary device within a single, limited range of orientations, or within a number of discrete, limited ranges of orientations. This feature is particularly advantageous because the retaining arm acts to at least partially determine the orientation of the ancillary device, as well as resist removal of the ancillary device from the port, in the retention configuration. Hence, separate formations for determining orientation are not necessary.

The retaining arm preferably includes formations that define the permitted orientations of the ancillary device relative to the port. In presently preferred embodiments, the retaining arm includes a channel adapted to receive a portion of the ancillary device, such that the ancillary device may adopt one of two permitted orientations, or an orientation within two limited ranges of permitted orientations, which are defined by the orientation of the channel relative to the port. In order to restrict the ancillary device to two pre-determined orientations, the ancillary device is preferably received within the channel with a close fit. For example, the ancillary device may have a hemi-cylindrical portion that is received within a corresponding, hemi-cylindrical channel of the retaining arm.

The retaining arm preferably also includes a closure for the port, such that the retaining arm is movable to a closed configuration in which the closure is engaged with the port. This feature is particularly advantageous because a separate closure for the port is not required, which reduces the risk of the closure becoming detached from the apparatus, and may also reduce manufacturing costs.

The closure is preferably adapted to engage the port, such that the port is sealed from ambient air. The closure may have the form of a plug, and may have an abutment at the periphery of the plug that abuts the port in the closed configuration. Alternatively, the closure may have the form of a sleeve that fits closely around the port, and an end wall that occludes the entrance to the port. The closure will typically have a generally circular cross-section.

The closure preferably projects from an operative surface of the retaining arm. The closure is preferably disposed between the portion of the retaining arm that engages the ancillary device and the end of the retaining arm about which the arm is rotatably mounted. The closure may be inclined relative to the portion of the retaining arm from which it projects. In this arrangement, the operative surface of the retaining arm may include an recess to accommodate at least part of the port in the closed configuration.

The enclosing wall is preferably generally tubular, and preferably defines a gas passageway suitable for inclusion, in-line, in a breathing circuit. In particular, the internal diameter of the enclosing wall is preferably about 15-25 mm, eg 22 mm. The enclosing wall preferably includes standard tubular connectors at each end of the gas passageway, which enable the device to be connected into a breathing circuit.

The port is preferably aligned generally orthogonally relative to the gas passageway, and is preferably aligned diametrically, and hence facing the centre of the interior of the gas passageway.

The component of a respiratory apparatus according to the invention is preferably a component of a breathing circuit. In particular, the component is preferably suitable for inclusion in an inhalation and/or exhalation limb of a breathing circuit.

According to a further aspect of the invention, there is provided a respiratory apparatus comprising a component as described above and an ancillary device, the ancillary device being adapted to be received in the port, such that the retaining arm acts to resist removal of the ancillary device from the port in its retention configuration.

The respiratory apparatus preferably includes a breathing circuit, and the component of a respiratory apparatus is preferably a component of the breathing circuit. In particular, the component preferably forms part of an inhalation and/or exhalation limb of the breathing circuit. The respiratory apparatus typically also includes a ventilator for delivering gases to an inhalation limb of the breathing circuit. The ventilator may also receive exhalation gases from an exhalation limb of the breathing circuit.

The component may be a connector for joining other components of a breathing circuit, such as breathing tubes, humidification chambers and/or other connectors, together. In a particular embodiment, the component is a connector for connecting an outlet of a humidification chamber and a breathing tube, which may be a heated wire breathing tube. This connector preferably has a first gas passageway for connection to the outlet of a humidification chamber, and a second gas passageway at an angle, eg about 90° or about 135°, to the first gas passageway for connection to a breathing tube, wherein the port is preferably provided in the first gas passageway, preferably adjacent to the interface with the second gas passageway. The second gas passageway may also include an opening adapted to receive an electrical connector for use with a heated wire breathing tube.

The ancillary device may be a sensor device, such as a sensor probe, particularly where the component of a respiratory apparatus according to the invention forms part of a breathing circuit. The sensor device typically comprises a sensor housing, at least a portion of which is adapted for engagement with the port. The sensor device preferably also includes a grip portion, which is suitable for being gripped by a user during engagement of the sensor device with the port. The grip portion is preferably adapted for engagement with the retaining arm and may, for example, have a generally hemi-cylindrical surface on the opposing side of the sensor device from the port.

A particular type of sensor device suitable for use with the invention comprises a grip portion that is arranged orthogonally relative to the sensor housing, for example in a T-shaped configuration.

The sensor device may include formations that cooperate with formations of the component of a respiratory apparatus to at least partially determine the orientation of the sensor device relative to the port. In particular, the cooperating formations may determine the particular orientation that may be adopted by the sensor from the discrete pre-determined orientations, or the discrete, limited ranges of orientations, permitted by the retaining arm. Alternatively, the sensor port may include an indicator that is aligned by the user with a corresponding indication on the component, eg on the port itself, to indicate a correct orientation of the sensor relative to the port, and hence relative to the gas passageway. The sensor may also include a stop formation, which determines the position of the sensor device relative to the port along the engagement axis.

The component of a respiratory apparatus according to the invention may be manufactured as a single, integral component. Typically, the component will be formed in plastics material, often by injection moulding.

According to a further aspect of the invention, there is provided a method of manufacturing a component of a respiratory apparatus, the method comprising injection moulding a component comprising a gas passageway defined by an enclosing wall, a port in the enclosing wall adapted to receive an ancillary device, and a retaining arm that is movable between an open configuration in which an ancillary device may be engaged with the port, and a retention configuration in which the retaining arm acts to resist removal of the ancillary device from the port.

The component is preferably formed in a single injection moulding process. The component may be formed monolithically from a single material. Alternatively, the component may be formed as a single, integral component, but consisting of two or more different materials. In particular, a multi-shot injection moulding or co-moulding technique may be used.

BRIEF DESCRIPTION OF THE FIGURES

A preferred embodiment of the invention will now be described in detail, with reference to the accompanying drawings, in which.

DETAILED DESCRIPTION OF THE INVENTION

Figure 1:
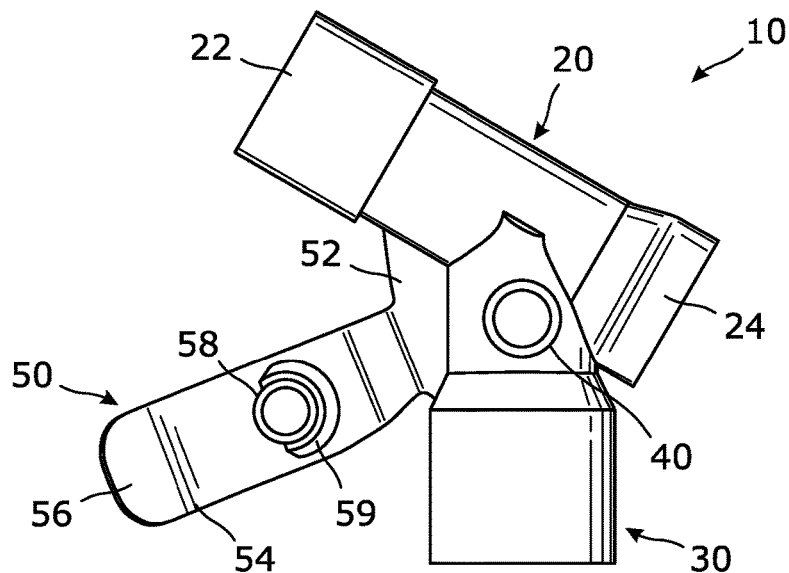
FIG. 1 is a side view of a connector according to the invention.
Figure 2:
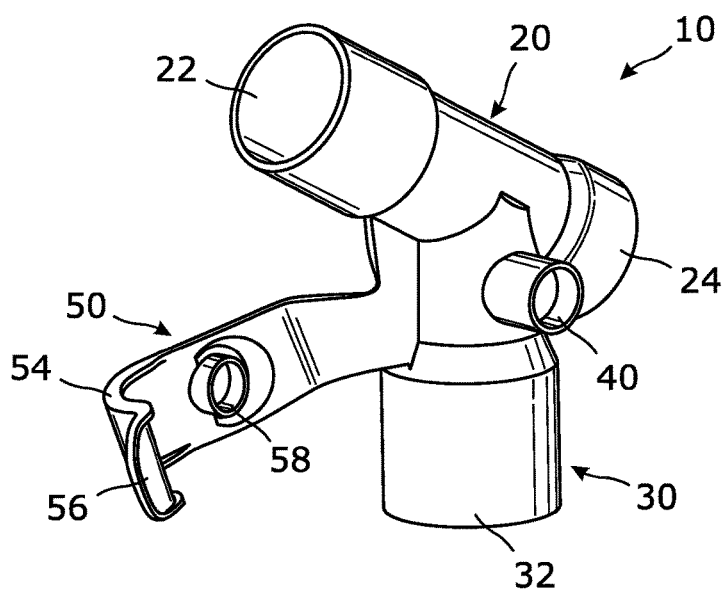
FIG. 2 is a perspective view of the connector according to the invention.

FIG. 1 shows a connector according to the invention, which is generally designated 10. The connector 10 is injection moulded in a suitable plastics material, as a single component, ie monolithically formed. The connector 10 comprises an upper gas passageway 20 and a lower gas passageway 30.

The connector 10 is shown in FIG. 1 in its orientation during use. In particular, the lower end of the lower gas passageway 30 is connected, in use, to the upwardly projecting outlet port of a humidification chamber, and the upper end of the upper gas passageway 20 is connected to a breathing tube for carrying humidified inhalation gases to the patient. References to "upper" and "lower" parts of the connector 10 in the following description refer to the connector 10 in the orientation shown in FIG. 1.

The upper gas passageway 20 and lower gas passageway 30 are generally tubular in form, with the lower gas passageway 30 extending from an opening in the wall of the upper gas passageway 20, and the upper gas passageway 20 and the lower gas passageway 30 being orientated at an angle of 135° to each other.

The upper end portion of the upper gas passageway 20 and the lower end portion of the lower gas passageway 30 define upper tubular connector 22 and lower tubular connector 32 that are each adapted to connect to other components of the breathing circuit, and in particular an inhalation breathing tube and an outlet port of a humidification chamber, respectively. The upper tubular connector 22 of the upper gas passageway 20 has the form of a male tubular connector, which has enlarged exterior dimensions relative to the remainder of the upper gas passageway 20 and a slightly tapered exterior. The lower tubular connector 32 of the lower gas passageway 30 has the form of a female tubular connector, which has enlarged interior and exterior dimensions relative to the remainder of the lower gas passageway 30 in order to accommodate the male connector of the component to which it connects.

The lower end portion 24 of the upper gas passageway 20 is open and has enlarged interior and exterior dimensions relative to the remainder of the upper gas passageway 20 in order to accommodate an electrical socket assembly (not shown in the Figures). In particular, the upper tubular connector 22 of the upper gas passageway 20 is adapted to be connected to a heated wire breathing tube, with an associated electrical socket assembly being mounted in the lower end portion 24 of the upper gas passageway 20.

In addition to the upper gas passageway 20 and the lower gas passageway 30, the connector 10 includes a port 40 adapted to receive an ancillary device, and in particular a sensor probe, and a retaining arm 50 for cooperation with the port 40 and the probe.

The port 40 is formed at the upper end of the lower gas passageway 30, immediately adjacent to the upper gas passageway 20. The port 40 comprises a circular aperture in the wall of the lower gas passageway 30, and a cylindrical collar that extends outwardly from the circular aperture. In particular, the cylindrical collar of the port 40 is orientated generally perpendicular to both the upper gas passageway 20 and the lower gas passageway 30.

The retaining arm 50 is hingedly mounted to a web of material, which is designated 52, formed between the exterior surfaces of the gas passageway 20 and the lower gas passageway 30. The web of material 52 is substantially planar, and in particular has width and length dimensions significantly greater than its thickness. Furthermore, the web of material 52 lies in the same plane as the central, longitudinal axes of the upper gas passageway 20 and the lower gas passageway 30.

The retaining arm 50 extends from an exposed edge of the web of material 52, where a region of material of reduced thickness defines a hinge, about which the retaining arm 50 is pivotable. The retaining arm 50 has an inner portion that is substantially planar and extends away from the hinge, its width gradually increasing away from the hinge. The inner portion extends into an intermediate portion, which is arranged at an angle to the inner portion, ie the intermediate portion extends out of the plane in which the inner portion lies. The intermediate portion includes a cylindrical plug 58 that projects from its operative surface.

The plug 58 is adapted to be received within the cylindrical collar of the port 40, such that the port 40 is closed and sealed from its surroundings. The plug 58 is orientated at an angle to the intermediate portion of the retaining arm 50, from which the plug 58 projects, and hence a semi-circular recess 59 is provided on the hinge-side of the plug 58 to accommodate the wall of the port 40 when the plug 58 is engaged therewith.

The intermediate portion of the retaining arm 50 extends into an outer portion of the retaining arm 50, which curves out of the plane of the intermediate portion and defines a near hemi-cylindrical channel 54 in its operative surface, which is open at each end. A lip 56 is provided at the end of the retaining arm 50, which is angled sharply away from the curved outer portion.

As discussed above, the lower end of the lower gas passageway 30 is connected, in use, to the upwardly projecting outlet port of a humidification chamber, and the upper end of the upper gas passageway 20 is connected to a breathing tube for carrying humidified inhalation gases to the patient. Furthermore, the breathing tube connected to the upper end of the upper gas passageway 20 is a heated wire breathing tube, which includes internal wires that are heated by an electrical supply provided by a control apparatus, through the connection provided by the electrical socket assembly at the lower end of the upper gas passageway 20.

The control apparatus typically utilizes data from a temperature sensor and a flow sensor, both inserted in the breathing circuit, to control the heated base and the heated wires. For example, a temperature sensor is typically inserted into the inhalation limb of the breathing circuit, at the patient end, and a flow sensor is typically inserted into the inhalation limb of the breathing circuit, at the humidification chamber end.

The connector 10 shown in the Figures is therefore adapted to receive a flow sensor probe, which measures the flow rate of the gases exiting the humidification chamber, and entering the inhalation breathing tube. The control apparatus utilizes the data from this flow sensor probe to enable appropriate control of the heated base and heated wires. At its most simple, this control may be to cease activation of the heated base and heated wires if a low flow rate, or indeed no flow rate at all, is detected, thereby preventing potentially dangerous overheating.

Figure 3:
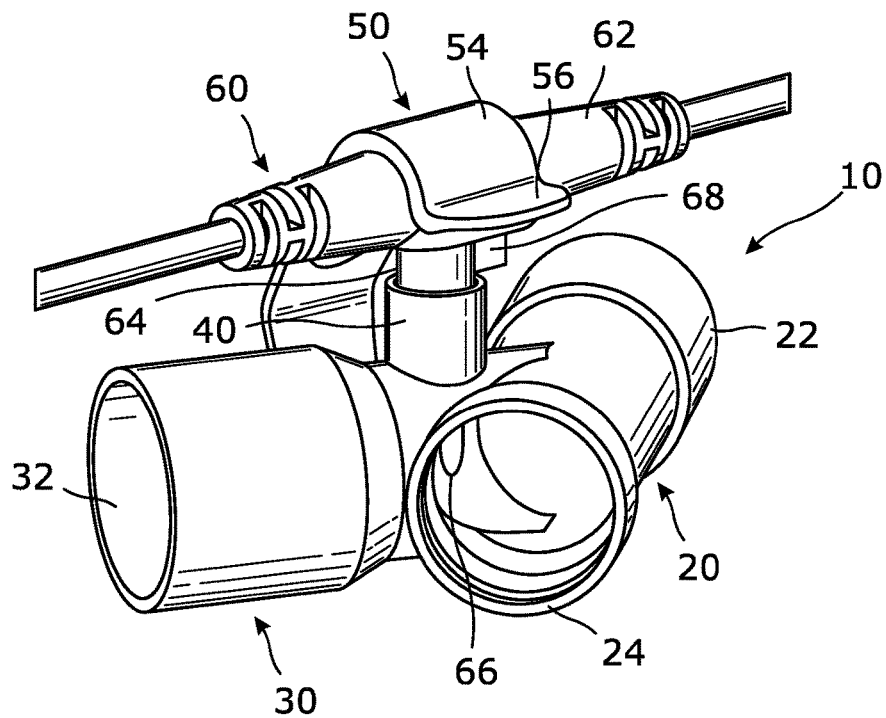
FIG. 3 is a perspective view of the connector in a closed configuration.
Figure 4:
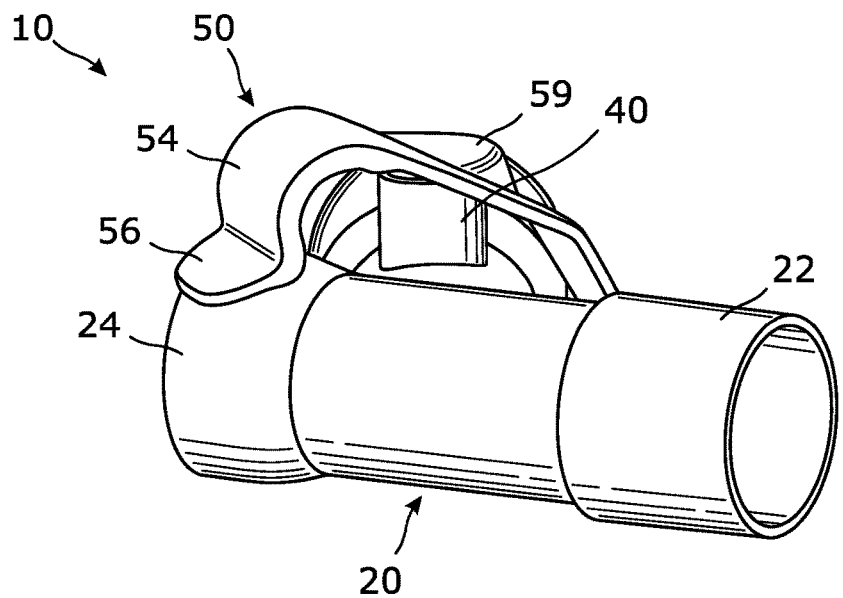
FIG. 4 is a perspective view of the connector with a probe assembled therewith.

The flow sensor probe is shown in FIG. 3 engaged with the port 40 of the connector 10, and is generally designated 60. The probe 60 comprises a generally cylindrical grip portion 62, which has electrical wires extending from each end. The probe 60 also includes a sensor housing 64 that extends perpendicularly from the cylindrical grip portion 62, to give the probe 60 a general T-shape. The sensor housing 64 has a cylindrical portion adapted to be received with a close fit within the cylindrical collar of the port 40, and two tapered end portions 66 (only one of which is visible in FIG. 3) that extend into the interior of the lower gas passageway 20, immediately adjacent to the interior of the upper gas passageway 30.

Once the probe 60 has been engaged with the port, such that the cylindrical grip portion 62 of sensor housing 64 is received with a close fit within the cylindrical collar of the port 40, the retaining arm 50 is rotated into engagement with the probe 60. In particular, the retaining arm 50 is rotated until the cylindrical grip portion 62 of the probe 60 is received within the near hemi-cylindrical channel 54 in the operative surface of the retaining arm 50. The retaining arm 50 is configured to prevent removal of the probe 60 from the port 40, unless the retaining arm 50 is rotated out of engagement with the probe 60.

In addition, due to the complementary nature of the channel 54 of the retaining arm 50 and the cylindrical grip portion 62 of the probe 60, the probe 60 can only adopt one of two possible orientations relative to the port 40. The sensor housing 64 of the probe 60 is provided with a lateral projection, in the form of a V-shaped tooth 68, and the port 40 is provided with a corresponding visual indication on the exterior of the port 40. In this way, the user chooses the orientation of the probe 60 in which the V-shaped tooth 68 is aligned with the corresponding indication on the exterior of the port 40, thereby ensuring that the probe 60 has the correct one of the two possible orientations that can be adopted.

Where the connector 10 is used in a breathing circuit that does not utilize a sensor probe in the port 40, the retaining arm 50 is adapted to be rotated into engagement with the port 40. In particular, the plug 58 is inserted into the cylindrical collar of the port 40, by means of rotation of the retaining arm 50, such that the port 40 is closed and sealed from its surroundings. The breathing circuit including the connector may then be used without any probe 60 being present in the port 40.

The invention claimed is:

1. A component of a respiratory apparatus comprising:
a first gas passageway angularly coupled to a second gas passageway in a branched configuration, wherein the first gas passageway is defined by an enclosing wall extending between an input opening and an opening into the second gas passageway, and the second gas passageway extends along a length between a first opening and a second opening;
a port in the enclosing wall adapted to receive an ancillary device, wherein the port extends in a transverse orientation from the first gas passageway; and
a retaining arm hingedly mounted at one end to an exterior surface of the component such that the retaining arm is movable between an open configuration in which the ancillary device may be engaged with the port, and a retention configuration in which the retaining arm acts, in use, to resist removal of the ancillary device from the port, wherein the entire retaining arm maintains substantially a same overall shape in both the open configuration and the retention configuration, and wherein the retaining arm is retained in the open configuration until a user manually moves the retaining arm into the retention configuration, wherein the retaining arm has an inner portion extending from an outer side of the enclosing wall, an intermediate portion formed next to the inner portion and angled with respect to the inner portion, and an outer portion formed next to the intermediate portion and curving out of a plane defined by the intermediate portion to provide a hemi-cylindrical channel in which the ancillary device is received when the retaining arm is in the retention configuration.

2. The component as claimed in claim 1, wherein the retaining arm is arranged not to impede engagement of the ancillary device with the port in its open configuration.

3. The component as claimed in claim 1, wherein the retaining arm is rotatable between the open and retention configurations.

4. The component as claimed in claim 1, wherein the retaining arm is engaged with an exterior surface of the ancillary device in the retention configuration.

5. The component as claimed in claim 1, wherein the retaining arm grips or captivates the ancillary device in the retention configuration.

6. The component as claimed in claim 5, wherein at least a portion of the retaining arm is formed of a resilient material and adapted to receive at least a portion of the ancillary device therewithin, such that receiving the ancillary device within the resilient portion of the retaining arm causes the resilient portion to deflect to accept the ancillary device during engagement, the resilient portion acting to grip or captivate the ancillary device on full engagement of the retaining arm with the ancillary device.

7. The component as claimed in claim 1, wherein the retaining arm is adapted to resist removal of the ancillary device from the port by location of a retaining portion of the arm on an opposing surface of the ancillary device relative to the port.

8. The component as claimed in claim 7, wherein the retaining arm is generally arcuate in overall shape.

9. The component as claimed in claim 1, wherein the retaining arm is arranged to remain in the retention configuration, and in particular in engagement with the ancillary device, on movement of the ancillary device in the direction of disengagement from the port.

10. The component as claimed in claim 9, wherein said movement of the ancillary device applies a force on the arm, and the force applied by the ancillary device on the arm is at an angle that does not result in rotation of the retaining arm to its open configuration.

11. The component as claimed in claim 1, wherein the retaining arm is rotatable about an axis that is generally perpendicular to the engagement axis of the port.

12. The component as claimed in claim 11, wherein the axis of rotation is offset laterally from the engagement axis of the port.

13. The component as claimed in claim 1, wherein the retaining arm is adapted to at least partially determine the orientation of the ancillary device relative to the port in the retention configuration.

14. The component as claimed in claim 13, wherein the retaining arm is adapted to permit orientation of the ancillary device in a single pre-determined orientation, or in a limited number of discrete pre-determined orientations, and/or the retaining arm is adapted to permit orientation of the ancillary device within a single, limited range of orientations, or within a number of discrete, limited ranges of orientations.

15. The component as claimed in claim 1, wherein the retaining arm includes a channel adapted to receive a portion of the ancillary device, such that the ancillary device may adopt one of two permitted orientations, or an orientation within two limited ranges of permitted orientations, which are defined by the orientation of the channel relative to the port.

16. The component as claimed in claim 15, wherein the ancillary device is received within the channel with a close fit.

17. The component as claimed in claim 1, wherein the retaining arm includes a closure for the port, such that the retaining arm is movable to a closed configuration in which the closure is engaged with the port.

18. The component as claimed in claim 17, wherein the closure is disposed between a portion of the retaining arm that engages the ancillary device and an end of the retaining arm about which the retaining arm is rotatably mounted.

19. The component as claimed in claim 1, wherein the component of the respiratory apparatus according to the invention is manufactured as a single, integral component.

20. A respiratory apparatus comprising a component as claimed in claim 1 and an ancillary device, the ancillary device being adapted to be received in the port, such that the retaining arm acts to resist removal of the ancillary device from the port in its retention configuration.

21. The respiratory apparatus as claimed in claim 20, wherein the respiratory apparatus includes a breathing circuit, and the component including the port and the retaining arm is a component of the breathing circuit.

22. The respiratory apparatus as claimed in claim 21, wherein the component including the port and the retaining arm forms part of an inhalation and/or exhalation limb of the breathing circuit.

23. The respiratory apparatus as claimed in claim 20, wherein the ancillary device is a sensor device.

24. The respiratory apparatus as claimed in claim 23, wherein the sensor device comprises a sensor housing, at least a portion of which is adapted for engagement with the port, and a grip portion, which is suitable for being gripped by a user during engagement of the sensor device with the port.

25. The respiratory apparatus as claimed in claim 24, wherein the grip portion is adapted for engagement with the retaining arm.

26. A method of manufacturing a component of a respiratory apparatus, the method comprising injection moulding a component comprising a first gas passageway angularly coupled to a second gas passageway in a branched configuration, wherein the first gas passageway is defined by an enclosing wall extending between an input opening and an opening in the second gas passageway, and the second gas passageway extends along a length between a first opening and a second opening, a port in the enclosing wall adapted to receive an ancillary device, wherein the port extends in a transverse orientation from the first gas passageway, and a retaining arm hingedly mounted at one end to an exterior surface of the component such that the retaining arm is movable between an open configuration in which an ancillary device may be engaged with the port, and a retention configuration in which the retaining arm acts, in use, to resist removal of the ancillary device from the port, wherein the entire retaining arm maintains substantially a same overall shape in both the open configuration and the retention configuration, and wherein the retaining arm is retained in the open configuration until a user manually moves the retaining arm into the retention configuration, wherein the retaining arm has an inner portion extending from an outer side of the enclosing wall, an intermediate portion formed next to the inner portion and angled with respect to the inner portion, and an outer portion formed next to the intermediate portion and curving out of a plane defined by the intermediate portion to provide a hemi-cylindrical channel in which the ancillary device is received when the retaining arm is in the retention configuration.

27. The method as claimed in claim 26, wherein the component is formed in a single injection moulding process.

28. The method as claimed in claim 26, wherein the component is formed monolithically from a single material.

29. The method as claimed in claim 26, wherein the component is formed as a single, integral component, but consisting of two or more different materials.

30. A respiratory apparatus comprising:
a component comprising:
a first gas passageway coupled to a second gas passageway at an obtuse angle, wherein the first gas passageway is defined by an enclosing wall extending between an input opening and an opening into the second gas passageway, and the second gas passageway extends along a length between a first opening and a second opening;
a port in the enclosing wall adapted to receive an ancillary device, wherein the port extends in a transverse orientation from the first gas passageway; and
a retaining arm hingedly mounted at one end to an exterior surface of the component such that the retaining arm is movable between an open configuration in which the ancillary device may be engaged with the port, and a retention configuration in which the retaining arm acts, in use, to resist removal of the ancillary device from the port, wherein the entire retaining arm maintains substantially a same overall shape in both the open configuration and the retention configuration, and wherein the retaining arm is retained in the open configuration until a user manually moves the retaining arm into the retention configuration; and
an ancillary device, the ancillary device being adapted to be received in the port with a tapered end of the ancillary device located in the first gas passageway, wherein the retaining arm acts to resist removal of the ancillary device from the port when the ancillary device is received in the port and the retaining arm is in the retention configuration, wherein the retaining arm has an inner portion extending from an outer side of the enclosing wall, an intermediate portion formed next to the inner portion and angled with respect to the inner portion, and an outer portion formed next to the intermediate portion and curving out of a plane defined by the intermediate portion to provide a hemi-cylindrical channel in which the ancillary device is received when the retaining arm is in the retention configuration.

31. A component of a respiratory apparatus comprising:
a first gas passageway defined by an enclosing wall;
a port in the enclosing wall adapted to receive an ancillary device, wherein the port extends in a transverse orientation from the first gas passageway; and
a retaining arm hingedly mounted at one end to an exterior surface of the component such that the retaining arm is movable between an open configuration in which the ancillary device may be engaged with the port, and a retention configuration in which the retaining arm acts, in use, to resist removal of the ancillary device from the port, wherein the entire retaining arm maintains substantially a same overall shape in both the open configuration and the retention configuration, and wherein the retaining arm is retained in the open configuration until a user manually moves the retaining arm into the retention configuration, wherein the retaining arm has an inner portion extending from an outer side of the enclosing wall, an intermediate portion formed next to the inner portion and angled with respect to the inner portion, and an outer portion formed next to the intermediate portion and curving out of a plane defined by the intermediate portion to provide a hemi-cylindrical channel in which the ancillary device is received when the retaining arm is in the retention configuration.

32. The component as claimed in claim 31, wherein the retaining arm includes a closure for the port at the intermediate portion whereby the retaining arm solely retains the ancillary device at the port in use and closes the port in non-use of the ancillary device.

* * * * *